United States Patent
Wildman

[11] Patent Number: 6,152,730
[45] Date of Patent: Nov. 28, 2000

[54] BITE REGISTRATION TRACING APPLIANCE WITH MOVABLE LOWER WING

[76] Inventor: Alexander J. Wildman, 6 Devon Mill Pl., The Woodlands, Tex. 77382

[21] Appl. No.: 09/357,202

[22] Filed: Jul. 20, 1999

Related U.S. Application Data

[60] Provisional application No. 60/094,534, Jul. 29, 1998.

[51] Int. Cl.[7] .................................................. A61C 19/04
[52] U.S. Cl. ................................. 433/68; 433/69; 433/215
[58] Field of Search .................................. 433/68, 69, 73, 433/215

[56] References Cited

U.S. PATENT DOCUMENTS

| | | | |
|---|---|---|---|
| 2,255,267 | 9/1941 | Moran | 433/69 |
| 2,612,688 | 10/1952 | Avary | 433/69 |
| 4,273,533 | 6/1981 | Della Croce . | |
| 4,964,769 | 10/1990 | Hass | 433/69 X |
| 4,981,437 | 1/1991 | Wilcox . | |
| 5,186,624 | 2/1993 | Gottsleben | 433/69 |
| 5,257,932 | 11/1993 | Leinfelder et al. . | |
| 5,336,087 | 8/1994 | Vogel et al. | 433/69 |
| 5,385,470 | 1/1995 | Polz . | |
| 5,632,619 | 5/1997 | Polz . | |
| 5,722,828 | 3/1998 | Halstrom . | |

OTHER PUBLICATIONS

Ball Bearing Bite Recorder Kit product information, 1995, 7 pages, Productivity Training Corporation, Morgan Hill, California.

*Primary Examiner*—Nicholas D. Lucchesi
*Attorney, Agent, or Firm*—Marger Johnson & McCollom, P.C.

[57] ABSTRACT

A bite registration appliance includes an upper base plate and a two-piece lower plate, one carrying a tracing stylus and the other carrying a tracing plate, for making a Gothic arch tracing in a patient having natural dentition without interfering with the patient's bite. One embodiment is arranged to fit within the arches, engaging undercut areas of the lingual sides of the arches, the lower plate being formed by two members that are movable laterally about a slot to engage extension wings against the inner sides of the mandible. In the second embodiment, both the maxillary and mandibular plates are two-piece units, each having a pair of arcuate extension arms that clamp around the lingual side of the patient's dental arches. The extension wings or arms in both embodiments fit loosely against a typical patient's archform and then custom fitted to the patient by trimming and molding a self-curing acrylic to the extension wings or arms. The plates are fixed to the lingual or labial sides of the patient's maxillary and mandibular arches and locked in place to make a tracing using locking screws or nuts, and then removed.

21 Claims, 3 Drawing Sheets

BITE REGISTRATION TRACING APPLIANCE WITH MOVABLE LOWER WING

RELATED APPLICATION DATA

This application claims priority from U.S. provisional application Ser. No. 60/094,534, filed Jul. 29, 1998.

BACKGROUND OF THE INVENTION

This invention relates to the alignment of a patient's dental occlusion and more particularly to a method and tool for alignment of mandibulary and maxillary arches containing natural dentition.

It is important in dentistry to be able to provide for the patient an ideal dental occlusion. When the teeth bite together, the condyles of the mandible should be guided into the fossa of the temporoman dibular joint in an ideal postural position. This is called centric relation. Some dentists become very good at manipulating the mandible with their hands into the ideal centric relation. This manipulation is an inexact art that is difficult to teach. It would be desirable to have a mechanical way to aid the dentist in this manipulation process.

A device called the Gothic-arch tracer has been used successfully in full-denture construction, as shown in FIGS. 1 and 2. In the edentulous patient, the upper and lower base plate 10, 16 is fitted to the edentulous ridges as a first step in denture construction. The lower base plate can carry the tracing pin 18 and the upper can carry the tracing plate 12. The Gothic-arch kit, with the component parts necessary for this full-denture technique, can be obtained from: Blue Dolphin Products, Concord Circle, Unit #1, Morgan Hill, Calif. 95037.

This Gothic-arch tracer has a tracing pin 18, which is usually attached by a support plate 20 into the lower dental arch. This pin occludes upon a striking plate or tracing plate secured into the upper arch. The pin can have some means to mark the upper plate as the mandible moves, while maintaining pressure on the upper plate. This produces tracing lines 14 on the tracer plate 12, which represent the movement patterns of the mandible.

The mandible is limited in its movements by the ligaments, muscles, and hard tissue of the temporomandibular joint. Movements of the mandible, marking the most extreme limited positions, are said to be border movements. When the Gothic-arch tracer inscribes lines on the upper plate, while moving from the most retruded position forward and laterally in the extreme border pattern, the tracing lines often take the shape of a Gothic arch, thus the name Gothic-arch tracer.

The apex of the Gothic-arch tracing represents the most retruded border position of the mandible. This point is called centric, and the mandible retruded into the centric point is said to be in centric relation.

When the teeth bite together in the most extreme closed position, they are said to be in centric occlusion. Many dentists believe that when the teeth are in centric occlusion, the mandible should be guided into the most retruded centric-relation position. When the centric position is located, it can be used to construct a bite-registration fixture, to be used to mount casts of the dental arches on the lab articulator, which simulates the patient's mouth. Dental appliances can then be constructed on the mounted cast. The occlusal biting surfaces of appliances constructed on such mounted casts will then guide the mandible in centric relation when seated in the mouth. The Gothic-arch mechanism can also be used to adjust the occlusion directly in the patient's mouth.

A device and method for using the Gothic-arch tracer in the natural teeth are described in U.S. Pat. No. 5,722,828 (Halstrom). The device described provides for bite rims fitted over the natural teeth, and secured with dental-impression material contained within the rims. These rims have a tracer screw and tracer plate mounted on arms which extend forward outside of the mouth. When the tracing is done, the two units are locked together in centric position, and removed from the mouth. Dental casts are then inserted into the resilient impression material for mounting on an articulator. The procedure is very time-consuming. The appliance is bulky. Placing the cast into the impression material in the rims can be less than accurate. The appliance, which covers the occlusal surface of the teeth, requires that the bite registration be taken with the teeth in an open-bite position. It is unable to take the bite registration in a nearly closed-bite position, i.e., with the occlusal surfaces of the teeth in a barely-missing-contact position.

Accordingly, a need remains for a better way to determine proper bite registration in a patient having natural teeth.

SUMMARY OF THE INVENTION

The object of this invention is to provide an easy-to-use means to locate and register the ideal centric bite-posture position of the mandible, when natural teeth are present.

A further object is to avoid obstructing the patient's bite during the bite registration process.

To use a Gothic arch tracer with existing teeth, the invention mounts the tracing pin or stylus and tracing plate on base units that leave the occlusal surfaces free. A wax bite registration can then be taken directly in the mouth in the normal way.

In one aspect of the invention, the tracing units can be located inside the dental arches. When securing base plates to the lingual surfaces of natural teeth, the presence of undercuts presents problems that must be considered and dealt with. Undercuts in tooth anatomy are those areas that will interfere with the insertion and removal of the appliance holding the tracing elements. Mild undercuts are desirable, because the resiliency of the base plates allows proper locking and release. Severe undercuts are not desirable. When there are severe undercuts, it becomes difficult or impossible to seat and remove a solid base appliance. When the undercuts are relieved, the appliance can become too loose. Placing the tracer plates on a base plate in the upper arch works well, because there are relatively few undercuts in the upper-lingual anatomy. Placing the tracer pin on a base-plate unit in the lower arch does not work well, because there are usually severe undercuts present. Therefore, there is a need to design a base-plate unit that can carry a Gothic-arch tracing unit, and can be easily locked into severe undercuts for maximum retention, then easily unlocked for removal. Such a unit would leave the occlusal surfaces free.

Another approach is to construct the upper and lower base units to engage the labial surfaces of the natural teeth. The Gothic-arch tracing units can be mounted on arms extending forward out of the mouth from the base units. The use of forward-extending arms is known in the prior art, but the base units always cover the occlusal surfaces of the natural teeth. In the appliance of the present invention, the labial base units would not cover the occlusal surfaces.

Therefore, one aspect of the invention would lock into the lingual anatomy of the dental arches, with the tracing apparatus placed inside the confines of the dental arches. The occlusal surfaces of the teeth would not be covered by the base units. In another aspect, there would be base units that would lock into the labial anatomy of the dental arches, with the Gothic-arch units borne on arms that would place the Gothic-arch tracers forward out of the mouth. The occlusal surface would not be covered by the base appliance.

One embodiment of the invention provides a two-piece appliance that is arranged to engage and lock into the lingual undercuts of the mandibular dental arch by moving laterally from the midline. The two pieces are locked with a lock nut. The appliance is unlocked by loosening the lock nut, so that the two base pieces can move away from the lingual surfaces toward the midline. One base member carries a centrally located, threaded post, which also contains internal threads which receive a tracer screw, which protrudes toward the upper arch. The base member has an eccentric pocket surrounding the post. The second base member is configured to fit into the pocket in the first base member, and also carries a slide, allowing the base member to fit over the post. The two base members are locked together by a nut screwed into the post. When the nut is loosened, the second base member is free to disengage from the pocket. The slot allows the second base member to slide toward the midline. The two base members contain peripheral extensions or wings, which fit into the inside surfaces of the lower teeth. The appliance is preferably made of acrylic, which can be modified in the lab to fit loosely inside the lower arch. The appliance is then custom fitted with self-curing acrylic.

In another embodiment of the invention, two two-piece base units are arranged to fit into the undercuts of the labial surface. One base member engages the right side of the dental arches, and the other fits around the left side of the dental arches. The units would be constructed for both the upper and lower dental arches. The units would move toward the midline to be locked into place. The units carry forward extensions that bear the Gothic-arch tracing mechanism. Pins can be placed either on the upper or the lower unit, and the tracing tables could be placed in apposition on either the upper or the lower units. The two members in both the upper and the lower arch would be locked together with threaded screws. Releasing these screws allows the base members to move laterally, disengaging the appliances. These units preferably are made of acrylic, so that they could be custom fitted in the laboratory using self-curing acrylic to engage the arches securely along the guideline.

The foregoing and other objects, features and advantages of the invention will become more readily apparent from the following detailed description of a preferred embodiment of the invention, which proceeds with reference to the accompanying drawings.

DETAILED DESCRIPTION

Figure 1:
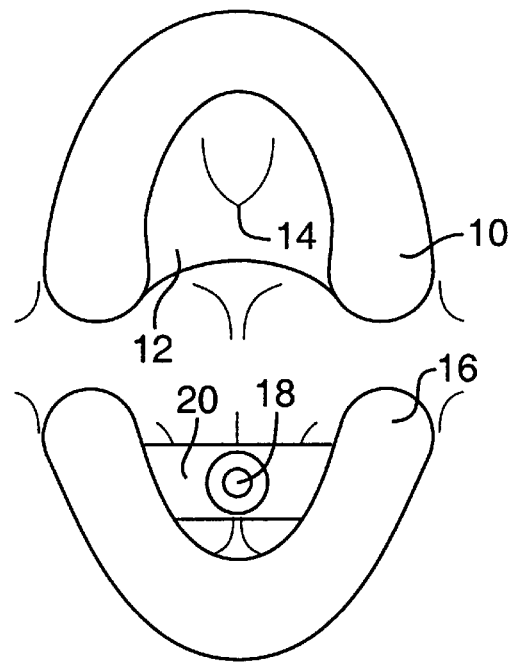
FIG. 1 is a top view of a prior art Gothic arch tracer mounted on full denture base plates.
Figure 2:
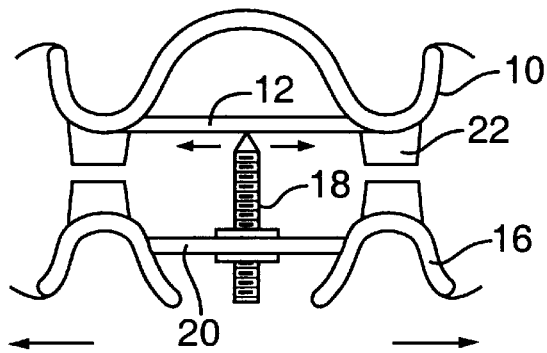
FIG. 2 is a cross-sectional view of the Gothic arch tracer of FIG. 1 mounted on full denture base plates.
Figure 3:
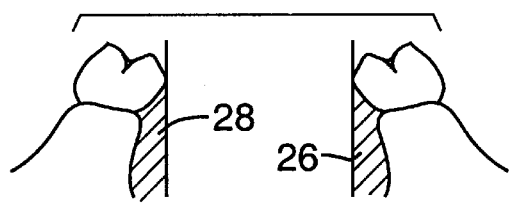
FIG. 3 is a cross-sectional view of the lower dental arch showing undercut areas.
Figure 4:
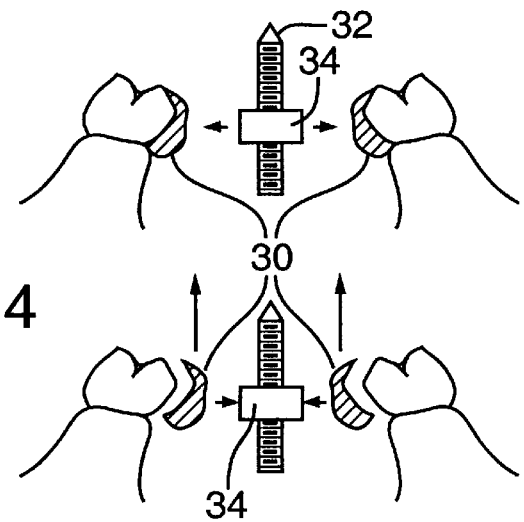
FIG. 4 is a schematic representation of a solution to the undercut problem.
Figure 5:
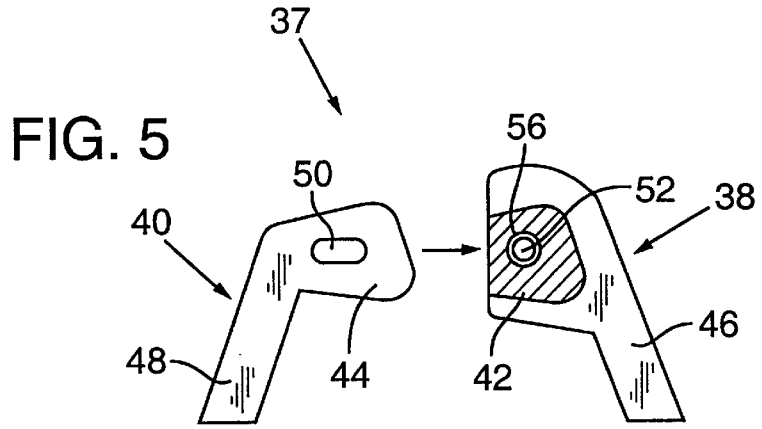
FIG. 5 is a top view of the two base plate members of one embodiment of the invention.
Figure 6:
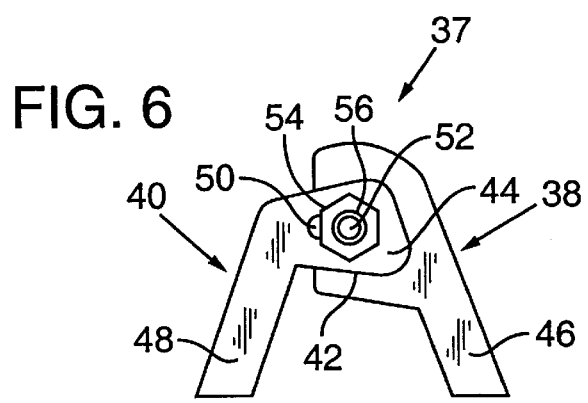
FIG. 6 is a top view of the base plate of FIG. 5 of the parts locked together.

FIGS. 3 and 4 show the general concept of the present invention. In contrast to the prior art as exemplified by FIGS. 1 and 2 for dentures and Halstrom for natural dentition, the present invention takes advantage of the mandibular anatomy adjacent the gum line to avoid blocking or interfering with the patient's occlusion. FIG. 3 shows the undercut areas 26, 28 along the lingual surfaces of the typical patient's mandibular arch. The invention utilizes these undercut areas to position and secure a plate structure 34 carrying a tracer stylus 32 by means of engagement devices 30 which are contoured to fit into the undercut areas. A device according the invention is designed to move the engagement means into and out of engagement with the mandibular arch to lock the plate structure 34 into place without blocking the occlusal surfaces of the teeth. This concept is shown in the context of a lingually-mounted base plate, a preferred embodiment of which is shown and described with reference to FIGS. 5–8. Alternatively, this concept can be applied to engaging the labial anatomy adjacent the gum line of both the mandible and maxilla to support a Gothic arch tracing unit outside the patient's mouth, again without blocking or interfering with the patient's occlusion. A second embodiment implementing this alternative technique is shown in FIG. 9.

FIRST EMBODIMENT

Figure 7:
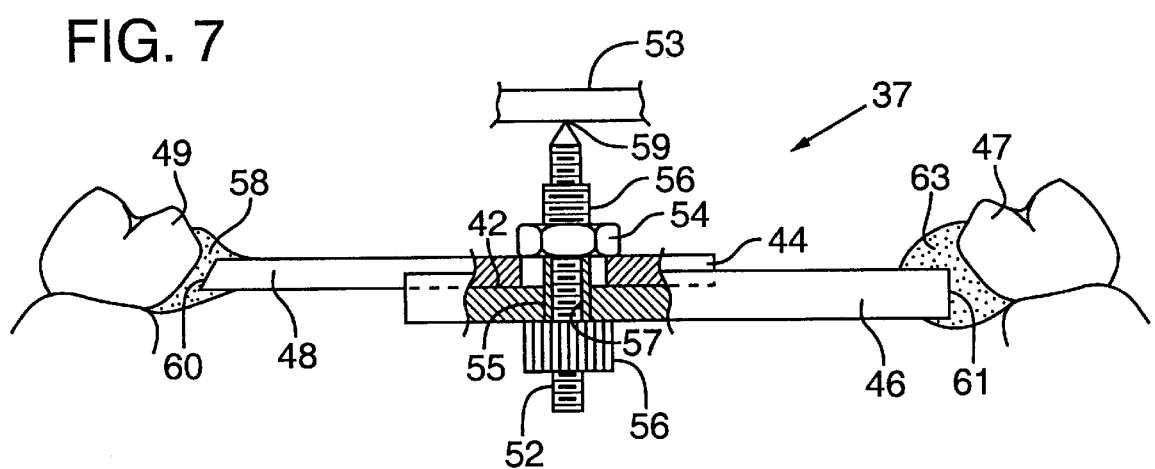
FIG. 7 is a cross-sectional view of the two members of FIG. 6 locked and custom fitted to the lingual surfaces of the lower teeth.

FIGS. 5–8, respectively, show a first embodiment of a Gothic-arch tracing device 37 in accordance with the invention. This tracing device has a base plate formed by first and second base members 38, 40, made of molded, machined or laminated plastic, preferably acrylic. The base member 38 has an eccentric pocket or recess 42. Within this pocket, the base member 38 is pierced by a centrally located internally-threaded hole 55 that receives an externally-threaded post 56 which has an internally-threaded hole 57. This threaded hole receives a tracing pin 52. The base member 38 bears a peripheral extension or wing 46 contoured to fit loosely into the corresponding lingual surfaces of the mandibular teeth 47. The peripheral edges of the wing can be trimmed in the lab to enhance the loose fitting arrangement 61 (FIG. 7). The loose fitting extension 46 can be custom fitted to the lingual surfaces of the undercut areas on one side of the mandibular arch in the laboratory with self-curing acrylic 63.

A second base member 40, also preferably formed of acrylic, is configured to fit into the pocket in the first base member 38 so as to be laterally movable and then secured in the pocket. This second member has a laterally-extending slot for movably receiving the post 56 and securing the second member in the pocket by tightening a lock nut 54 that is threaded on the post 56, as shown in FIG. 7. The second base member has a peripheral extension 48 that fits loosely into the corresponding lingual surfaces of the mandibular teeth 49. Extensions 46, 48 are mutually positioned in the assembled device so as to fit loosely within a generally U-shaped arch form. The loose fit of the lateral extension can be enhanced by trimming in the lab. The extension can be custom fitted to the undercut areas of an opposite side of the arch with self-curing acrylic 58.

Figure 8:
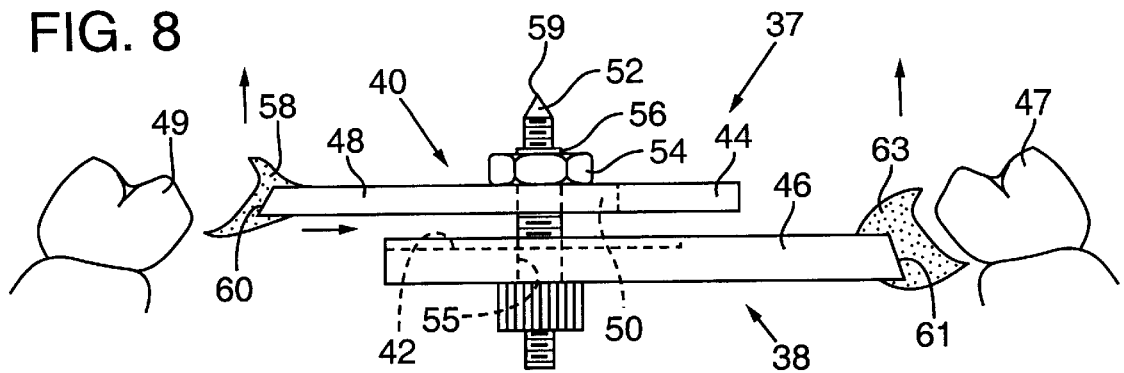
FIG. 8 is a cross-sectional view of the two members of FIG. 7 unlocked and slid toward the midline.

The base members of the unit 37 can be unlocked and disengaged by loosening the lock nut 54, allowing the second base member 40 to move out of the pocket 42 as shown in FIG. 8. The configuration of the slot 50 allows the second base member 40 to move laterally toward the midline, thereby disengaging the tracer unit 37 from the lingual surfaces of the mandibular arch, as shown in FIG. 8.

The threaded tracing pin 52 can be adjusted so that the Gothic arch tracing can be recorded at the desired vertical dimension. In its simplest form, the pin can be a sharpened point 59 that can scratch a tracing on a plastic maxillary tracing plate 53.

SECOND EMBODIMENT

Figure 9A:
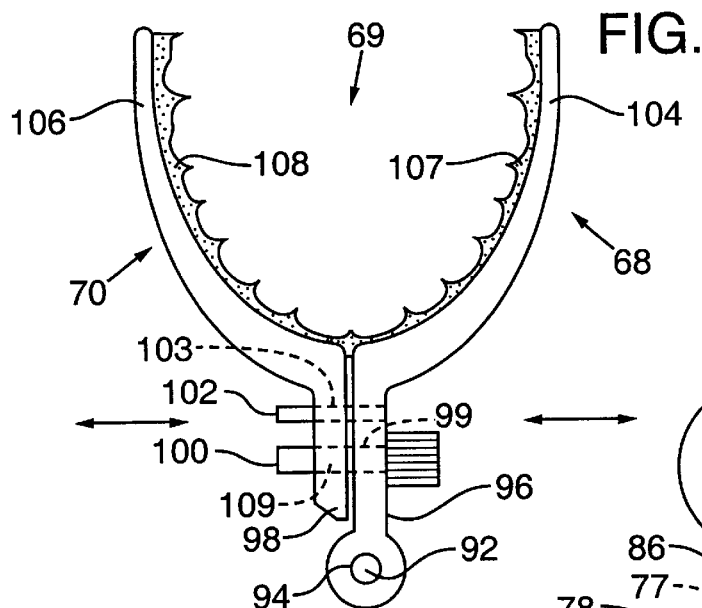
FIGS. 9A and 9B are top views of a second embodiment of the invention custom fitted to engage the labial surfaces of the upper and lower dental arches.
Figure 9B:
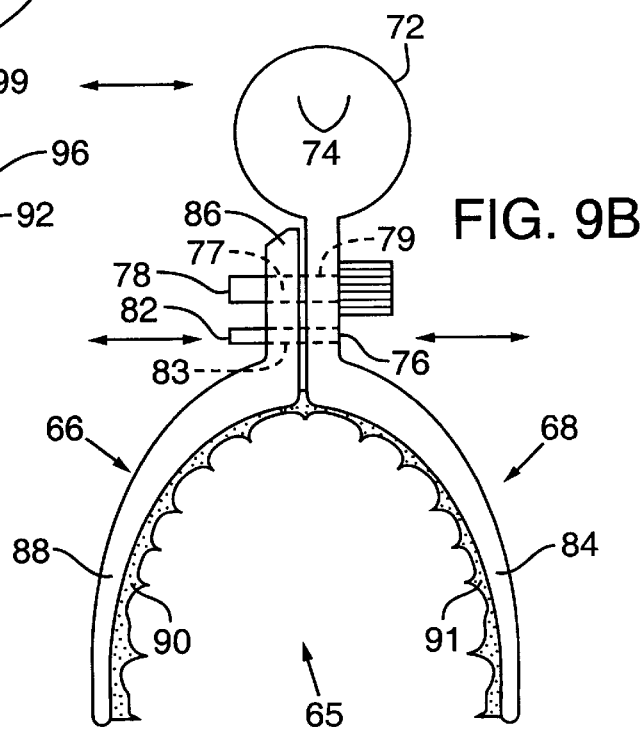

A second embodiment of the invention implemented as a two-piece maxillary unit 69 and a two-piece mandibular unit 65 are shown in FIGS. 9A and 9B. These units are arranged to engage the labial surfaces of the upper and lower teeth and support the Gothic arch tracing plate 72 and tracing pin or stylus 92 anteriorly of the patient's mouth.

The mandibular unit 65 of the second embodiment of the invention has a right-hand member 64 and a left-hand member 66 that meet in the midline. Member 64 has an arcuate extension 84 that is configured to fit loosely around the labial anatomy of the right mandibular dental arch. The right-hand member 64 has an anterior projection 76 that extends forward out of the mouth to end in a circular tracing plate 72 for making a Gothic arch tracing 74. The projection 76 has a lateral unthreaded hole 79 that receives a lock screw 78. An index pin 82 extends laterally toward the midline. The left-hand member 66 of the mandibular tracing unit 65 has an arcuate extension 88 configured to loosely fit the labial anatomy of the left side of the mandibular dental arch. The left side 66 also has an anterior projection 86 with an index hole 83 that receives the index pin 82 of the right-hand member 64. The projection 86 also has a threaded hole 77 to receive the lock screw 78.

When the lock screw 78 is tightened, the two halves 64 and 66 of the mandibular unit 65 move toward the midline engaging the labial surface of the mandibular arch. The arch extensions 84 and 88 can be custom fitted in the lab with self-curing acrylic. When the lock pin 78 is loosened, the two halves of the unit 65 can move laterally, disengaging the unit.

The maxillary unit 69 of the second embodiment of the invention has a right-hand member 70 and a lefthand member 68. The member 68 of the maxillary unit 69 has an arcuate extension or arm 104 that loosely fits against the labial surfaces of the left side of the maxillary arch. This extension ends at the midline with a projection arm 96 extending anteriorly out of the mouth. The end of this anterior extension is pierced with a threaded hole 94 that receives a threaded tracing pin 92. In its simplest form, the tracing pin can have a sharpened point that will produce the Gothic-arch tracing 74 on the tracing plate 72. The arm 96 has a lateral unthreaded hole 99 that receives a threaded lock screw 100. The arm 96 has an index pin 102 that extends laterally toward the midline. A second member 70 of the maxillary unit 69 has an arcuate extension 106 that is configured to loosely engage the labial surfaces of the right-hand side of the maxillary dental arch. Member 70 has a projection arm 98 that extends anteriorly out of the mouth along the midline along arm 96. This projection arm has an index hole 103 that accepts the index pin 102 and a threaded hole 109 that receives the lock screw 100. The arch extensions 106 and 107 can be custom fitted in the lab with self-curing acrylic. When the lock screw is tightened, the two halves 68 and 70 move toward the midline, engaging the labial surfaces of the maxillary arch. When the lock screw 100 is loosened, the two halves of unit 69 can move laterally, disengaging the unit.

The mandibular and maxillary units are preferably made of acrylic or another plastic material which is trimmable and to which a self-curing resin is bondable. The arcuate extensions 84, 88, 104 and 106 can be custom fitted in the lab with self-curing acrylic.

Having described and illustrated the principles of the invention in two preferred embodiments thereof, it should be apparent that the invention can be modified in arrangement and detail without departing from such principles. For example, in the first embodiment 37 any number of orthodontic expansion arrangements could be utilized. In the second embodiment unit 69 and 65 could have a snap-fit arrangement, replacing the lock screw. Any functional arrangement that would provide the necessary engagement and disengagement could be used. I claim all modifications and variations coming within the spirit and scope of the claims.

What is claimed is:

1. A bite registration method for determining a centric relationship of a patient's mandibular and maxillary arches, each arch including natural teeth protruding from the patient's gumline in a generally U-shape arrangement, the method comprising:

fitting a first base plate to the patient's maxillary arch, the first base plate including a Gothic-arch tracing table;

forming a two-part second base plate to fit the patient's mandibular arch, the second base plate comprising first and second movably-interconnected members and a Gothic-arch tracing stylus;

shaping the first and second members of the second base plate to fit into undercut areas adjoining a junction of the natural teeth and the gumline of the mandible;

positioning the first and second members of the second base plate laterally to engage within the undercut areas on opposite sides of the patient's mandibular arch, thereby securing the second base plate to the mandibular arch while leaving occlusal surfaces of the patient's natural teeth exposed;

moving the patient's mandible relative to the maxilla to effect relative movement of the base plates and the Gothic-arch tracing table and stylus carried by the base plates to make a Gothic arch tracing which locates the centric relationship of the patient's mandible and maxilla.

2. A bite registration method according to claim 1 including moving the patient's mandible with the base plates in place and the mandible in a nearly closed-bite position.

3. A bite registration method according to claim 2 including moving the patient's mandible to make the Gothic-arch tracing in multiple-height bite-opening positions.

4. A bite registration method according to claim 1 including locking the first and second members of the second base plate in a position spread laterally apart in the mandibular arch preparatory to making the Gothic arch tracing.

5. A bite registration method according to claim 4 including unlocking the first and second members of the second base plate and moving the members laterally together toward the midline for removal of the second base plate from the mandibular arch after making the Gothic arch tracing.

6. A bite registration method according to claim 1 in which:
the forming step includes preforming the first and second members to an approximate arch form fitting roughly into a lingual anatomical mandibular arch of the patient's natural teeth; and
the shaping step includes applying a self-curing resin to each of the first and second members and molding the resin to the lingual anatomy of the patient's mandibular arch.

7. A bite registration method according to claim 1 including locking the first and second members of the second base plate in a clamped position laterally together in the mandibular arch preparatory to making the Gothic arch tracing.

8. A bite registration method according to claim 7 including unlocking the first and second members of the second base plate and moving the members laterally apart for removal of the second base plate from the mandibular arch after making the Gothic arch tracing.

9. A bite registration device for determining a centric relationship of a patient's mandibular and maxillary arches, each arch including natural teeth protruding from the patient's gumline in a generally U-shaped arrangement, the device comprising:
a first base plate sized and arranged to fit to the patient's maxillary arch;
a two-part second base plate arranged to fit to the patient's mandibular arch, the second base plate comprising first and second movably-interconnected members; and
a Gothic-arch tracing table and stylus mounted on the first and second base plates;
the first and second members of the base plate being sized and shaped to fit into undercut areas adjoining a junction of the natural teeth and the gumline of the mandible;
the first and second members of the base plate being laterally movable to engage within the undercut on opposite sides of the patient's mandibular arch to secure the second base plate to the mandibular arch while leaving occlusal surfaces of the patient's natural teeth exposed so that movement of the patient's mandible relative to the maxilla makes a Gothic arch tracing to locate the centric relationship of the patient's mandible and maxilla.

10. A bite registration device according to claim 9 in which said first and second members are interconnected by threaded post and a locking nut.

11. A bite registration device according to claim 10 in which the threaded post includes a stylus.

12. A bite registration device according to claim 10 in which the threaded post includes an internally-threaded bore for receiving a threaded stylus.

13. A bite registration device according to claim 9 in which a post is threaded into the first member, the second member includes a slot for receiving the post; and a nut is received on the post for clamping the first and second members together.

14. A bite registration device according to claim 13 in which the slot is oriented to enable lateral positioning of the first and second members.

15. A bite registration device according to claim 9 in which the first and second members are formed of a rigid plastic material that can be trimmed.

16. A bite registration device according to claim 15 in which the plastic material is bondable with self-curing dental acrylic resin.

17. A bite registration device according to claim 15 in which the plastic material includes acrylic.

18. A bite registration device according to claim 9 in which the first and second members are shaped to fit inside the mandibular arch.

19. A bite registration device according to claim 9 in which the first and second members are shaped to fit outside the mandibular arch.

20. A bite registration device according to claim 19 in which said tracing table is mounted on the second base plate.

21. A bite registration device according to claim 9 in which the first base plate is formed of first and second members arranged to fit outside the patient's maxillary arch.

* * * * *

UNITED STATES PATENT AND TRADEMARK OFFICE
CERTIFICATE OF CORRECTION

PATENT NO. : 6,152,730
DATED : November 28, 2000
INVENTOR(S) : Alexander J. Wildman It is certified that error appears in the above-identified patent and that said Letters Patent is hereby corrected as shown below:

Column 7,
Line 17, change "apart" to -- toward a midline --.

Signed and Sealed this

Twenty-ninth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,152,730
APPLICATION NO. : 09/357202
DATED : November 28, 2000
INVENTOR(S) : Alexander J. Wildman It is certified that error appears in the above-identified patent and that said Letters Patent is hereby corrected as shown below:

<u>Title page,</u>
Item [57], ABSTRACT,
Line 12, change "lingual" to -- labial --.

Signed and Sealed this

Twentieth Day of June, 2006

JON W. DUDAS
*Director of the United States Patent and Trademark Office*